United States Patent [19]

Hargreaves et al.

[11] Patent Number: 4,873,254
[45] Date of Patent: Oct. 10, 1989

[54] 1,4-DIHYDROPYRIDINES SUBSTITUTED BY 3-ARYLOXY-2-HYDROXYPROPYL AMINO MOIETY IN THE 4-PHENYL GROUP

[75] Inventors: Rodney B. Hargreaves, Poynton; Bernard J. McLoughlin; Stuart D. Mills, both of Macclesfield, all of England

[73] Assignee: Imperial Chemical Industries plc, London, England

[21] Appl. No.: 828,363

[22] Filed: Feb. 11, 1986

[30] Foreign Application Priority Data

Feb. 11, 1985 [GB] United Kingdom ............... 8503425

[51] Int. Cl.$^4$ ............... C07D 211/86; A61K 31/455
[52] U.S. Cl. .................... 514/356; 514/338; 514/318; 514/255; 514/332; 514/339; 514/312; 514/333; 514/236.2; 546/321; 546/271; 546/194; 546/158; 546/272; 546/256; 546/273; 546/263; 546/270; 544/131; 544/365
[58] Field of Search ............... 546/321, 271, 194, 158, 546/272, 256, 273, 263, 270; 514/356, 338, 318, 255, 232, 332, 236, 339, 312, 333; 544/365, 131

[56] References Cited

U.S. PATENT DOCUMENTS 4,500,527 2/1985 Loev et al. .................... 514/223

FOREIGN PATENT DOCUMENTS 0167371 6/1985 European Pat. Off.
1409865 10/1975 United Kingdom.
1425059 2/1976 United Kingdom.

OTHER PUBLICATIONS

J. J. Baldwin et al., "Approches to Vasodilating-/Beta–Adrenergic Blocking Agents: Examples of the Dihydrolutidine Type", Journal of Medicinal Chemistry, vol. 24, No. 5, pp. 628-631, May 1981.

Primary Examiner—Jane T. Fan
Attorney, Agent, or Firm—Cushman, Darby & Cushman

[57] ABSTRACT

A dihydropyridine of the formula:

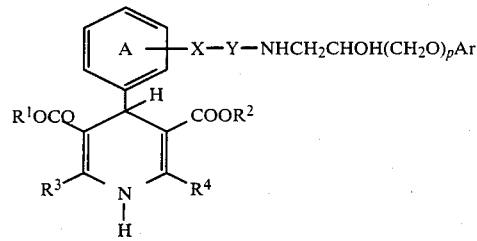

wherein $R^1$ and $R^2$ each is alkyl, alkenyl or alkoxyalkyl, wherein $R^3$ and $R^4$ each is alkyl, wherein benzene ring A is unsubstituted or bears one or more additional substituents selected from halogeno, cyano, nitro, trifluoromethyl and alkyl, or bears the substituent =N—O—N= attached to the 5- and 6-positions, wherein Ar is as defined in the specification, wherein p is 0 or 1, wherein X is —O— or —S—, and wherein Y is straight-or branched-chain alkylene or alkenylene each of 2 to 12 carbon atoms which may optionally be interrupted by one or two groups selected from oxygen, sulphur, imino, substituted imino, phenylene, substituted phenylene, pyridylene, cycloalkylene, 1,4-piperazinediyl, 1,4-piperidinediyl and amido groups; or an acid-addition salt thereof, processes for their manufacture and pharmaceutical compositions containing them. The compounds possess either beta-adrenergic blocking or calcium ion slow channel blocking properties, or both such properties, and may be used in the treatment of hypertension.

13 Claims, No Drawings

1,4-DIHYDROPYRIDINES SUBSTITUTED BY 3-ARYLOXY-2-HYDROXYPROPYL AMINO MOIETY IN THE 4-PHENYL GROUP

This invention relates to new alkanolamine derivatives and more particularly it relates to new dihydropyridine derivatives which possess antihypertensive properties.

Many 2,6-dialkyl-4-aryl-1,4-dihydropyridine-3,5-dicarboxylate derivatives are known which inhibit the movement of calcium ions in the cardiovascular system of warm-blooded animals, and which thereby produce an antihypertensive effect. The most-used of these is nifedipine, which is dimethyl 1,4-dihydro-2,6-dimethyl-4-o-nitrophenylpyridine-3,5-dicarboxylate.

Also known are many 1-aryloxy-3-amino-propan-2-ol derivatives which possess beta-adrenergic receptor blocking properties and which also produce an antihypertensive effect. Two of the most-used of these are propranolol and atenolol, which are respectively 1-(naphth-1-yloxy)- and 1-p-carbamoylmethylphenoxy-3-isopropylaminopropan-2-ol.

One described attempt to combine these two types of chemical structure into one molecule is reported by Merck workers in the Journal of Medicinal Chemistry, 1981, Vol. 24, pages 628 to 631, in which a 3-amino-2-hydroxypropoxy substituent was introduced into the 4-aryl substituent of a 4-aryl-1,4-dihydropyridine derivative, without much success in producing a compound with antihypertensive activity of the type sought by the authors.

More recently, since the priority date of the present application, U.S. Specification No. 4500527 has been published describing similar compounds in which the 3-amino-2-hydroxypropoxy substituent is linked to the 4-aryl substituent by the group —CH=N—, such compounds being claimed to have antihypertensive and beta-adrenergic blocking properties.

We have now found that compounds which do possess useful antihypertensive activity may be obtained by suitably combining a 3-aryloxy-2-hydroxypropylamino moiety with a 1,4-dihydropyridine moiety.

According to the present invention there is provided a dihydropyridine of the formula:

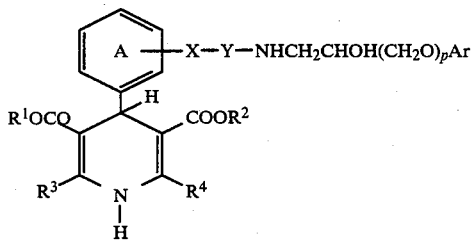

wherein $R^1$ and $R^2$, which may be the same or different, each is alkyl, alkenyl or alkoxyalkyl each of up to 6 carbon atoms; wherein $R^3$ and $R^4$, which may be the same or different, each is alkyl of up to 6 carbon atoms; wherein benzene ring A is unsubstituted or bears one or more additional substituents selected from halogeno, cyano, nitro, trifluoromethyl and alkyl of up to 6 carbon atoms, or bears the substituent

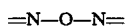

attached to the 5- and 6-positions (that is, to form a benzo-2,1,3-oxadiazole nucleus); wherein Ar is phenyl, naphthyl, tetrahydronaphthyl, indanyl or indenyl which is unsubstituted or which bears one or more substituents selected from halogeno, trifluoromethyl, hydroxy, amino, nitro, carbamoyl and cyano, and alkyl, alkenyl, alkoxy, alkenyloxy, alkoxyalkoxy, alkylthio, alkanoyl, carbamoylalkyl, alkanoylaminoalkylcarbamoylalkoxy and alkanoylamino each of up to 6 carbon atoms, and arylalkoxy of up to 10 carbon atoms; or Ar is a 5- or 6-membered heterocyclic ring containing 1, 2 or 3 heteroatoms selected from oxygen, nitrogen and sulphur, which ring is saturated or unsaturated, which ring is unsubstituted or bears one or more substituents selected from oxo, halogeno, trifluoromethyl, phenyl and morpholino, and alkyl and alkoxy each of up to 6 carbon atoms, and arylalkyl of up to 12 carbon atoms, and which ring may also be fused to a benzene ring, Ar being joined to the rest of the molecule either from the heterocyclic ring or from the fused benzene ring; wherein p is 0 or 1; wherein X is —O— or —S—; and wherein Y is straight- or branched-chain alkylene or alkenylene each of 2 to 12 carbon atoms which may optionally be interrupted by one or two groups selected from oxygen (—O—), sulphur (—S—), imino and substituted imino (—NR$^5$ wherein $R^5$ is hydrogen, alkyl or alkanoyl each of up to 10 carbon atoms, phenyl or aralkyl of up to 12 carbon atoms), phenylene, substituted phenylene, pyridylene, cycloalkylene of up to 6 carbon atoms, 1,4-piperazinediyl, 1,4-piperidinediyl and amido (—CONH— or —NHCO—) groups; or an acid-addition salt thereof.

It will be observed that the dihydropyridine derivative of the invention may possess at least two asymmetric carbon atoms, namely the carbon atom of the —CHOH— group in the alkanolamine chain, and, when $R^1$ and $R^2$, or $R^3$ and $R^4$, are different, the carbon atom at the 4-position of the dihydropyridine nucleus, and it can therefore exist in racemic and optically-active forms. It is to be understood that this invention encompasses the racemic form of the dihydropyridine derivative and any optically-active form which possesses antihypertensive activity, it being a matter of common general knowledge how a racemic compound may be resolved into optically-active forms, and how the antihypertensive activity of these forms may be determined. It is further to be understood that beta-adrenergic blocking activity usually predominates in that optically-active form which has the "S" absolute configuration of the said —CHOH— group in the alkanolamine chain when p is 1 and the "R" absolute configuration when p is 0.

A suitable value for $R^1$, $R^2$, $R^3$, $R^4$, $R^5$ or a substituent in benzene ring A or Ar when it is alkyl is, for example, methyl, ethyl, isopropyl or isobutyl.

A suitable value for $R^1$ or for a substituent in Ar when it is alkenyl is, for example, allyl.

A suitable value for $R^1$ or $R^2$ when it is alkoxyalkyl is, for example, methoxyethyl, ethoxyethyl or propoxyethyl.

A suitable halogeno substituent in the benzene ring A or in Ar is, for example fluoro, chloro or bromo.

A suitable value for the alkoxy, alkenyloxy, alkoxyalkoxy, alkylthio, carbamoylalkyl, alkanoylaminoalkylcarbamoylalkoxy, alkanoylamino or arylalkoxy substituent in Ar is, for example, methoxy, ethoxy, propoxy, isopropoxy, allyloxy, methoxyethoxy, methylthio, carbamoylmethyl, N-(2-acetamidoethyl)carbamoylmethoxy, acetamido or benzyloxy.

A suitable value for $R^5$ when it is alkanoyl, or for an alkanoyl substituent in Ar is, for example, formyl, acetyl or benzoyl.

A suitable value for $R^5$ when it is aralkyl, or for an aralkyl substituent in Ar is, for example, benzyl.

A suitable value for Ar when it is heterocyclic, either single ring or benzo-fused ring, is, for example, 4-morpholino-1,2,5-thiadiazol-3-yl, 1-methyl-4-indolyl, 2-oxo-1,2,3,4-tetrahydro-5-quinolyl, 4-indolyl, 4-carbazolyl, 4-benzo[b]thienyl, 7-benzo[b]furanyl, 5-benzo[1,4]dioxanyl or 3-cyano-2-pyridyl.

A suitable value for Y is, for example, straight-chain alkylene of the formula $(-CH_2)_n-$, wherein n is an integer from 2 to 12; or $-(CH_2)_mC(CH_3)_2-$; or $-CH_2CH=CHCH_2-$; or $-(CH_2)_m-NH-(CH_2)_n-$ or $-(CH_2)_mNHCH_2C(CH_3)_2-$ or $-(CH_2)_m-N(CH_3)-(CH_2)_n-$ or $-(CH_2)_m-O(CH_2)_n-$ or

or $-(CH_2)_m-CONH-(CH_2)_n-$ wherein m and n, which may be the same or different, each is 2, 3, 4 or 5; or $A^1-CONH-A^2-CONH-(CH_2)_n$ wherein $A^1$ and $A^2$, which may be the same or different, each is $(CH_2)_m$, wherein m is 1 or 2, or $-C(CH_3)_3-$, and wherein n is 2 or 3; or

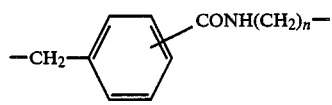

or $-CH_2CONH(CH_2)_n-$ wherein n is 2, 3, 4 or 5;

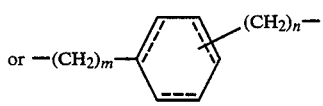

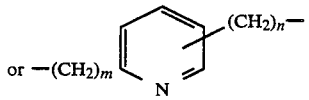

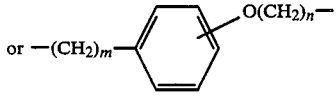

and wherein m and n, which may be the same or different, each is 1, 2, 3 or 4 and wherein the double bonds in the carbocyclic ring are optional (that is, cyclohexylene- or phenylene-bis-alkylene).

A suitable acid-addition salt of a dihydropyridine derivative of the invention is, for example, a salt derived from an inorganic acid, for example a hydrochloride, hydrobromide, phosphate or sulphate, or a salt derived from an organic acid, for example an oxalate, lactate, succinate, tartrate, acetate, salicylate, citrate, benzoate, beta-naphthoate or adipate.

A preferred dihydropyridine of the invention has the formula stated above wherein $R^1$ and $R^2$, which may be the same or different, each is alkyl of up to 4 carbon atoms or allyl, wherein $R^3$ and $R^4$ are both methyl, wherein the benzene ring A is unsubstituted or bears a nitro substituent, wherein Ar is phenyl which is unsubstituted or which bears one or two substituents selected from fluoro, chloro, bromo, hydroxy, nitro, cyano, alkyl, alkenyl, alkoxy, alkenyloxy and alkanoyl each of up to 4 carbon atoms, or Ar is 1,4-benzodioxan-5-yl, benzo[b]fur-7-yl or 4-morpholino-1,2,5-thiadiazol-3-yl, wherein p is 0 or 1, wherein X is $-O-$ or $-S-$ and wherein Y is straight- or branched-chain alkylene of up to 8 carbon atoms which may optionally be interrupted by one or two groups selected from oxygen, imino, phenylene and amido ($-CONH-$) groups, or Y is straight-chain alkenylene of up to 6 carbon atoms, or is an acid-addition salt thereof.

A particularly preferred dihydropyridine of the invention has the formula stated above wherein $R^1$ and $R^2$, which may be the same or different, each is methyl or ethyl, wherein $R^3$ and $R^4$ are both methyl, wherein the benzene ring A bears a nitro substituent in the 5-position and the side-chain in the benzene ring A is in the 2-position, wherein Ar is phenyl which is unsubstituted or which bears a single fluoro, chloro, bromo, nitro, cyano, allyl, methoxy, ethoxy, propoxy, isopropoxy, allyloxy or acetyl substituent in the 2-position, or Ar is 1,4-benzodioxan-5-yl, wherein p is 1, wherein X is $-O-$ and wherein Y is straight- or branched-chain alkylene of up to 8 carbon atoms which may optionally be interrupted by one oxygen or imino group, or one or more amido ($-CONH-$) groups, or one phenylene group, or one phenylene-oxy- group, or is an acid-addition salt thereof.

Specific dihydropyridine derivatives of the invention are hereinafter described in the Examples. Of these, preferred compounds are diethyl 4-[2-(N-{N-[2-(3-o-cyanophenoxy-2-hydroxypropylamino)ethyl]carbamoylmethyl}carbamoylmethoxy-5-nitrophenyl]-1,4-dihydro-2,6-dimethylpyridine-3,5-dicarboxylate; diethyl 4-{2-[4-(3-o-cyanophenoxy-2-hydroxypropylamino)butoxy]-5-nitrophenyl}-1,4-dihydro-2,6-dimethylpyridine-3,5-dicarboxylate; dimethyl 1,4-dihydro-4-{2-[4-(2-hydroxy-3-phenoxypropylamino)butoxy]-5-nitrophenyl}-2,6-dimethylpyridine-3,5-dicarboxylate and the corresponding (2-hydroxy-3-o-methoxyphenoxypropylamino)-, (3-o-ethoxyphenoxy-2-hydroxypropylamino)- and (2-hydroxy-3-o-propoxyphenoxypropylamino)-analogues thereof; dimethyl 1,4-dihydro-4-{2-[3-(2-hydroxy-3-phenoxypropylamino)-3-methylbutoxy]-5-nitrophenyl}-2,6-dimethylpyridine-3,5-dicarboxylate; dimethyl 1,4-dihydro-4-(2-{3-[2-(2-hydroxy-3-o-methoxyphenoxypropylamino)ethoxy]benzyloxy}-5-nitrophenyl)-2,6-dimethylpyridine-3,5-dicarboxylate; ethyl methyl 1,4-dihydro-4-{2-[4-(2-hydroxy-3-o-methoxyphenoxypropylamino)butoxy]-5-nitrophenyl}-2,6-dimethylpyridine-3,5-dicarboxylate; and dimethyl 1,4-dihydro-4-{2-[4-(2-hydroxy-3-o-methoxyphenoxypropylamino)but-trans-2-enyloxy]-5-nitrophenyl}-2,6-dimethylpyridine-3,5-dicarboxylate; and especially the (S)-enantiomers of the above compounds in respect of the asymmetrical carbon atom at the 2-position of the (2-hydroxy-3-(optionally-substituted)phenoxypropylamino)-group.

The dihydropyridine derivatives of the invention may be manufactured by any chemical process known to be useful for the manufacture of chemically-analogous compounds.

One preferred process for the manufacture of a dihydropyridine derivative of the invention comprises the reaction of an amine of the formula:

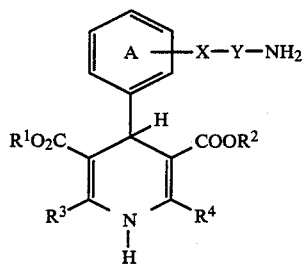

wherein A, $R^1$, $R^2$, $R^3$, $R^4$, X and Y have the meanings stated above, with an epoxide of the formula:

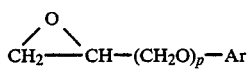

wherein Ar and p have the meanings stated above, or when p is 0, with a haloketone of the formula HalCH$_2$CO—Ar wherein Ar has the meaning stated above and where Hal stands for a halogeno group, for example bromo, followed by reduction, for example with sodium borohydride, of the aminoketone thus obtained.

The reaction may be carried out in an alcoholic diluent or solvent, for example in isopropanol, at a temperature of up to the boiling point of said diluent or solvent.

A second preferred process for the manufacture of a dihydropyridine derivative of the invention wherein the group —Y— is alkylene interrupted as stated above comprises joining the two parts of the molecule at the point of interruption of Y. Thus, for example, when Y is alkylene interrupted by an amido group —CONH—, the process comprises the reaction of an acid of the formula:

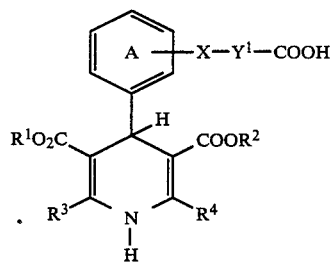

wherein A, $R^1$, $R^2$, $R^3$, $R^4$ and X have the meanings stated above, or an activated derivative thereof, with an amine of the formula:

H$_2$N—Y$^2$—NHCH$_2$CHOH(CH$_2$O)$_p$Ar wherein Ar and p have the meanings stated above, and wherein Y$^1$ and Y$^2$ are such that —Y$^1$—CONH—Y$^2$— has the same meaning as stated above for Y.

A third process for the manufacture of a dihydropyridine of the invention comprises the reaction of a compound of the formula:

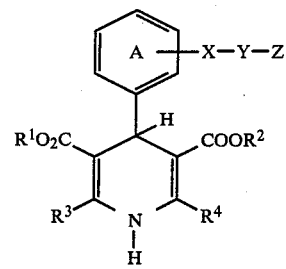

wherein A, $R^1$, $R^2$, $R^3$, $R^4$, X and Y have the meanings stated above and wherein Z stands for a displaceable group, with an amine of the formula:

H$_2$NCH$_2$CHOH(CH$_2$O)$_p$—Ar wherein Ar and p have the meanings stated above.

A suitable value for Z is, for example, a halogeno group, for example a bromo or chloro group, or a sulphonyloxy group, for example a methanesulphonyloxy or p-toluenesulphonyloxy group.

A fourth process for the manufacture of a dihydropyridine of the invention comprises the reaction of an aldehyde of the formula

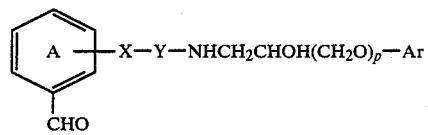

wherein A, X, Y, Ar and p have the meanings stated above, an aminocrotonate of the formula

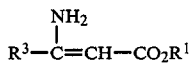

wherein $R^1$ and $R^3$ have the meanings stated above and a ketoacid derivative of the formula

R$^4$COCH$_2$COOR$^2$ wherein $R^2$ and $R^4$ have the meanings stated above.

This process may be carried out in a diluent or solvent at an elevated temperature, conditions conventionally used for the Hantszch synthesis of dihydropyridines. It is to be understood that when $R^1$ and $R^2$ are the same and $R^3$ and $R^4$ are the same the aminocrotonate may be replaced by an additional amount of the ketoacid derivative together with an ammonium salt, for example ammonium acetate.

As stated above, the dihydropyridine derivatives of the invention possess antihypertensive activity. This may be demonstrated by the ability of the compound to reduce the blood pressure of a spontaneously hypertensive rat, or of a rat made hypertensive by treatment with deoxycorticosterone acetate, or of a dog made hypertensive by the Goldblatt technique of unilateral nephrectomy and clipping of the contralateral kidney. These are all standard tests used to demonstrate antihypertensive effects of medicaments.

Some of the dihydropyridine derivatives of the invention possess beta-adrenergic blocking properties, some of them possess calcium ion slow-channel blocking properties and some of them possess both such activities. A preferred dihydropyridine derivative of the invention possesses both such activities. Beta-adrenergic blocking activity may be demonstrated in vivo by the ability of the compound to inhibit isoprenaline-induced tachycardia in a rat or cat, or in vitro by shifting to the right the dose-response curve of a guinea pig atrium to isoprenaline. Calcium ion slow channel blocking activity may be demonstrated in vitro by the ability of the compound to reduce spontaneous contraction in a rat portal veing preparation. These also are all standard tests used to demonstrate the stated activities.

Because of the beta-adrenergic blocking and/or calcium slow channel blocking properties of a dihydropyridine of the invention may also be useful in the treatment of heart diseases such as angina pectoris and cardiac arrhythmias.

At doses of a dihydropyridine derivative which produce effective antihypertensive activity in a rat or dog no symptom of toxicity is apparent.

The dihydropyridine derivative of the invention may be administered to warm-blooded animals, including man, in the form of a pharmaceutical composition comprising as active ingredient at least one dihydropyridine derivative of the invention, or an acid-addition salt thereof, in association with a pharmaceutically-acceptable diluent or carrier therefor.

A suitable composition is, for example, a tablet, capsule, aqueous or oily solution or suspension, dispersible powder, spray or aerosol formulation.

The pharmaceutical composition may contain, in addition to the dihydropyridine derivative of the invention, one or more drugs selected from sedatives, for example phenobarbitone, meprobamate, chloropromazine and the benzodiazepine sedative drugs, for example chlordiazepoxide and diazepam; vasodilators, for example glyceryl trinitrate, pentaerythritol tetranitrate, isosorbide dinitrate and hydralazine; diuretics, for example chlorthalidone, bendrofluazide, hydrochlorothiazide and chlorothiazide; other antihypertensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; and alpha-adrenergic blocking agents, for example phentolamine.

When used for the treatment of heart diseases, for example angina pectoris and cardiac arrhythmias, or for the treatment of hypertension in man, it is expected that the dihydropyridine derivative would be given to man at a local oral dose of between 20 mg. and 600 mg. daily, or an intravenous dose of between 1 mg. and 20 mg.

Preferred oral dosage forms are tablets or capsules containing between 10 and 100 mg., and preferably 10 mg. or 50 mg., of active ingredient. Preferred intravenous dosage forms are sterile solutions of the dihydropyridine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

A mixture of N-[2-(3,5-diethoxycarbonyl-1,4-dihydro-2,6-dimethylpyrid-4-yl)-4-nitrophenoxyacetyl]glycine (1.01 g.), 1-(2-aminoethylamino)-3-o-cyanophenoxypropan-2-ol (0.47 g.), 1-hydroxybenzotriazole (0.297 g.), dicyclohexylcarbodiimide (0.453 g.) and methylene chloride (50 ml.) was stirred at laboratory temperature for 18 hours, cooled to 0° C. and filtered, and the solid residue was washed with ice-cold methylene chloride. The combined filtrate and washings were washed with aqueous 2N-sodium bicarbonate solution, dried and evaporated to dryness and the residue was purified by flash chromatography on a silica gel column (Merck 9385, 100 g.) using an 80:20:3 v/v/v mixture of ethyl acetate, methanol and concentrated aqueous ammonia solution as eluant. The product was stirred with ethyl acetate and the mixture was filtered, and there was thus obtained diethyl 4-[2-(N-{N-[2-(3-o-cyanophenoxy-2-hydroxypropylamino)ethyl]carbamoylmethyl}carbamoylmethoxy)-5-nitrophenyl]-1,4-dihydro-2,6-dimethylpyridine-3,5-dicarboxylate, m.p. 194°–197° C.

The glycine derivative used as starting material was prepared as follows:

A mixture of 2-(3,5-diethoxycarbonyl-1,4-dihydro-2,6-dimethylpyrid-4-yl)-5-nitrophenoxyacetic acid (8 g.), ethyl glycinate hydrochloride (2.5 g.), 1-hydroxybenzotriazole (2.41 g.), dicyclohexylcarbodiimide (3.68 g.), triethylamine (2.48 ml.) and methylene chloride (200 ml.) was stirred at laboratory temperature for 18 hours, cooled to 0° C. and filtered, and the solid residue was washed with ice-cold methylene chloride. The combined filtrate and washings were washed with aqueous 2N-sodium bicarbonate solution, dried and evaporated to dryness and the residue was crystallised from methanol. There was thus obtained diethyl 4-[2-(N-ethoxycarbonylmethyl)carbamoylmethoxy-5-nitrophenyl]-1,4-dihydro-2,6-dimethylpyridine-3,5-dicarboxylate, m.p. 203°–206° C.

A mixture of a solution of the above ester (4.5 g.) in ethanol (150 ml.) and aqueous 3N-sodium hydroxide solution (2.81 ml.) was stirred at laboratory temperature for 18 hours and evaporated to dryness under reduced pressure, and the residue was partitioned between ethyl acetate (100 ml.) and aqueous 2N-sodium bicarbonate solution (100 ml.). The mixture was filtered, the solid residue being retained, and the layers of the filtrate were separated. The organic layer was extracted twice with aqueous 2N-sodium bicarbonate solution (50 ml. each time), and the combined aqueous layer, aqueous washings and a solution of the solid residue in water (200 ml.) were acidified with aqueous 2N-hydrochloric acid. The mixture was extracted three times with ethyl acetate (150 ml. each time) and the combined extracts were dried and evaporated to dryness. There was thus obtained as residue N-[2-(3,5-diethyoxycarbonyl-1,4-dihydro-2,6-dimethyl-pyrid-4-yl)-4-nitrophenoxyacetyl]glycine, m.p. 237°–239° C.

EXAMPLE 2

The process described in Example 1 was repeated using the appropriate carboxylic acid and the appropriate 1-(2-aminoethylamino)-3-aryloxypropan-2-ol as starting materials and there were thus obtained as oils the compounds described in the following table, the structures of all of which were confirmed by elemental analysis and proton magnetic resonance spectroscopy:

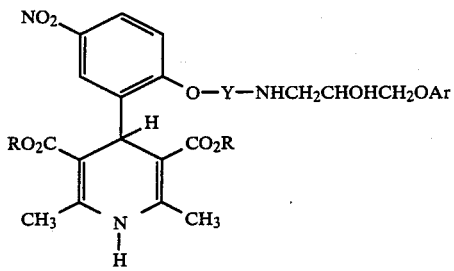

| R | Y | Ar |
|---|---|---|
| ethyl | CH₂CONHCH₂CONHCH₂CH₂ | 2-methoxyphenyl |
| methyl | CH₂CONHCH₂CONHCH₂CH₂ | 2-cyanophenyl |
| methyl | CH₂CONHCH₂CH₂CONHCH₂CH₂ | 2-cyanophenyl |
| ethyl | CH₂CH₂CH₂CONHCH₂CH₂ | 1,4-benzodioxan-5-yl |

The starting materials for the first three compounds were prepared by a similar process to that described in the second part of Example 1. Intermediates which were characterised by melting point have the formula:

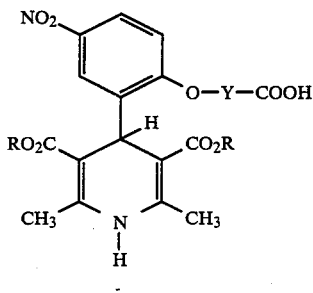

| R | Y¹ | m.p. (°C.) |
|---|---|---|
| methyl | CH₂CONHCH₂COOC₂H₅ | 215–217 |
| methyl | CH₂CONHCH₂CH₂COOC₂H₅ | 202–204 |
| ethyl | CH₂CH₂CH₂COOC₂H₅ | 139–141 |
| ethyl | CH₂CH₂CH₂COOH | 196–198 |

The last two compounds in the second table above were intermediates for the fourth compound in the first table above, and were prepared by initial reaction of 5-nitrosalicylaldehyde (16.7 g.), sodium hydride (2.64 g. of a 50% dispersion in oil), ethyl 4-bromobutyrate (15.74 g.) and dimethylformamide (200 ml.) at 100° C. for 4 hours, and then reaction of the 2-(3-ethoxycarbonylpropoxy)-5-nitrobenzaldehyde (m.p. 61°-62° C.) thus obtained (1.5 g.), ethyl acetoacetate (1.0 ml.), ammonium acetate (0.36 g.) and pyridine (25 ml.) at 100° C. for 5 hours.

EXAMPLE 3

A mixture of dimethyl 4-[2-(4-aminobutoxy)-5-nitrophenyl]-1,4-dihydro-2,6-dimethylpyridine-3,5-dicarboxylate (0.35 g.), phenylglycidyl ether (0.12 g.) and isopropanol (10 ml.) was heated under reflux for 3.5 hours and then evaporated to dryness, and the residue was purified by flash chromatography on a silica gel (Merck 9385) column using an 80:20:3 v/v/v mixture of ethyl acetate, methanol and concentrated aqueous ammonia solution as eluant. The product was crystallised from a mixture of ethyl acetate and petroleum ether (b.p. 60°-80° C.) and there was thus obtained dimethyl 1,4-dihydro-4-{2-[4-(2-hydroxy-3-phenoxypropylamino)butoxy]-5-nitrophenyl}-2,6-dimethylpyridine-3,5-dicarboxylate, m.p. 117°-120° C.

The dimethyl pyridine-3,5-dicarboxylate used as starting material was obtained as follows:

A stirred mixture of 5-nitrosalicylaldehyde (8.36 g.), potassium carbonate (11.04 g.), potassium iodide (0.2 g.), N-(4-bromobutyl)phthalimide (15.6 g.) and dimethylformamide (120 ml.) was heated at 100° C. for 48 hours and then cooled to laboratory temperature. Saturated aqueous sodium chloride solution (1200 ml.) and ethyl acetate (300 ml.) were added and the mixture was shaken and filtered, the solid residue being retained. The layers of the filtrate were separated, the aqueous layer was extracted with ethyl acetate (200 ml.) and the combined ethyl acetate solutions were washed three times with saturated aqueous sodium chloride solution (100 ml. each time), dried over magnesium sulphate and evaporated to dryness. The combined residue and retained solid were crystallised from methanol and there was thus obtained 5-nitro-2-(4-phthalimidobutoxy)benzaldehyde, m.p. 145°-148° C.

A stirred mixture of the above aldehyde (5.68 g.), methyl 3-aminocrotonate (1.92 g.), methyl acetoacetate (1.79 g.) and isopropanol (30 ml.) was heated under reflux for 40 hours, cooled to laboratory temperature and the liquid was decanted from the precipitated gum. The gum was stirred with diethyl ether and the mixture was filtered, and the liquid was kept at laboratory temperature for 18 hours and then filtered. The combined solid residues were crystallised from isopropanol and there was thus obtained dimethyl 1,4-dihydro-2,6-dimethyl-4-[2-(4-phthalimidobutoxy)-5-nitrophenyl]-pyridine-3,5-dicarboxylate, m.p. 119°-123° C.

A mixture of the above compound (1.8 g.), hydrazine hydrate (1.8 ml.) and ethanol (35 ml.) was heated under reflux for 18 hours, kept at laboratory temperature for 18 hours and then filtered. The filtrate was evaporated to dryness and the residue was crystallised from ethanol. There was thus obtained dimethyl 4(-8) 2-(4-aminobutoxy)-5-nitrophenyl]-1,4-dihydro-2,6-dimethyl-pyridine-3,5-dicarboxylate, m.p. 200°-202° C.

EXAMPLE 4

The process described in Example 3 was repeated using the appropriate 4-(2-aminohydrocarbyloxyphenyl)pyridine and the appropriate epoxide as starting materials, and there were thus obtained the compounds described in the following tables. If the compounds were not crystalline and therefore characterised by melting point, the structures were confirmed by elemental analysis, mass spectroscopy and proton magnetic resonance spectroscopy.

TABLE I

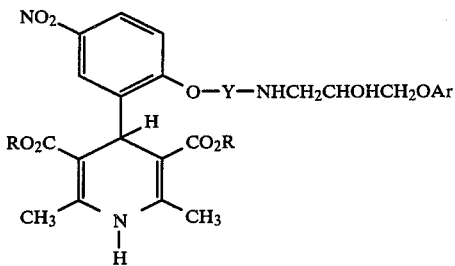

| R | Y | Ar | m.p. (°C.) |
|---|---|---|---|
| Et | $(CH_2)_3$ | phenyl | 117–120 |
| Et | $(CH_2)_4$ | phenyl | 122–126 |
| Me | $(CH_2)_4$ | 2-fluorophenyl | 129–132 |
| Me | $(CH_2)_4$ | 2-chlorophenyl | 144–146 |
| Et | $(CH_2)_4$ | 2-chlorophenyl | 128–131 |
| Me | $(CH_2)_4$ | 2-bromophenyl | 127–130 |
| Me | $(CH_2)_4$ | 2,4-dichlorophenyl | (oil) |
| Me | $(CH_2)_4$ | 4-hydroxyphenyl | 162–163 |
| Me | $(CH_2)_4$ | 2-nitrophenyl | 74–77 |
| Et | $(CH_2)_4$ | 2-nitrophenyl | 163–166 |
| Me | $(CH_2)_4$ | 2-cyanophenyl | (oil) |
| Et | $(CH_2)_4$ | 2-cyanophenyl | 185–188 |
| Me | $(CH_2)_4$ | 3-tolyl | 142–144 |
| Me | $(CH_2)_4$ | 2-allylphenyl | (oil) |
| Me | $(CH_2)_4$ | 2-methoxyphenyl | 130–132.5 |
| Et | $(CH_2)_4$ | 2-methoxyphenyl | 135–138 |
| Me | $(CH_2)_4$ | 4-methoxyphenyl | 153.5–156 |
| Me | $(CH_2)_4$ | 2-ethoxyphenyl | 116–119 |
| Me | $(CH_2)_4$ | 2-propoxyphenyl | 121–122 |
| Me | $(CH_2)_4$ | 2-isopropoxyphenyl | 81–83 |
| Me | $(CH_2)_4$ | 2-allyloxyphenyl | 132–134.5 |
| Et | $(CH_2)_4$ | 2-allyloxyphenyl | 109–112 |
| Me | $(CH_2)_4$ | 2-benzyloxyphenyl | 149–150.5 |
| Me | $(CH_2)_4$ | 2-acetylphenyl | (oil) |
| Me | $(CH_2)_4$ | 2-[N—(2-acetamido-ethyl)carbamoyl-methoxy]phenyl | (oil) |
| Me | $(CH_2)_4$ | 1,4-benzodioxan-5-yl | 144–147 |
| Et | $(CH_2)_4$ | 1,4-benzodioxan-5-yl | 148–151 |
| Me | $(CH_2)_4$ | 4-morpholino-1,2,5-thiadiazol-3-yl | (oil) |
| Me | $(CH_2)_4$ | benzofuran-7-yl | 161–162.5 |
| Me | $(CH_2)_5$ | phenyl | (oil) |
| Et | $(CH_2)_5$ | phenyl | (oil) |
| Me | $(CH_2)_5$ | 2-chlorophenyl | (oil) |
| Me | $(CH_2)_5$ | 2-cyanophenyl | (oil) |
| Et | $(CH_2)_5$ | 2-cyanophenyl | 175–178.5 |
| Me | $(CH_2)_5$ | 2-methoxyphenyl | 107–110 |
| Et | $(CH_2)_5$ | 2-methoxyphenyl | (oil) |
| Me | $(CH_2)_6$ | phenyl | 101–104 |
| Me | $(CH_2)_6$ | 2-cyanophenyl | 104–107 |
| Et | $(CH_2)_6$ | 2-cyanophenyl | 152–156 |
| Me | $(CH_2)_6$ | 2-methoxyphenyl | (oil) |
| Me | $(CH_2)_6$ | 1,4-benzodioxan-5-yl | (oil) |
| Me | $(CH_2)_7$ | phenyl | 113–117 |
| Me | $(CH_2)_7$ | 2-chlorophenyl | 121–124 |
| Me | $(CH_2)_7$ | 2-cyanophenyl | 118–122 |
| Et | $(CH_2)_7$ | 2-cyanophenyl | 161–164 |
| Me | $(CH_2)_7$ | 2-methoxyphenyl | (oil) |
| Me | $-CH_2CH_2C(CH_3)_2-$ | phenyl | (oil) |
| Me | $-(CH_2)_3C(CH_3)_2-$ | 2-methoxyphenyl | 124–127 |
| Me | $-CH_2(1,4\text{-phenylene})CH_2CH_2-$ | phenyl | 114–118 |
| Me | $-CH_2(1,4\text{-phenylene})CH_2CH_2-$ | 2-cyanophenyl | 156–157 |
| Me | $-CH_2(1,4\text{-phenylene})CH_2CH_2-$ | 2-methoxyphenyl | 119–121 |
| Me | $-CH_2(1,3\text{-phenylene})CH_2CH_2-$ | 2-cyanophenyl | (oil) |
| Me | $-CH_2(1,2\text{-phenylene})CH_2CH_2-$ | phenyl | (oil) |
| Me | $-CH_2(1,4\text{-phenylene})OCH_2CH_2-$ | 2-cyanophenyl | (oil) |
| Me | $-CH_2(1,3\text{-phenylene})OCH_2CH_2-$ | phenyl | (oil) |
| Me | $-CH_2(1,3\text{-phenylene})OCH_2CH_2-$ | 2-cyanophenyl | (oil) |
| Me | $-CH_2(1,3\text{-phenylene})OCH_2CH_2-$ | 2-methoxyphenyl | (oil) |
| Me | $-CH_2(1,3\text{-phenyl-}OCH_2CH_2CH_2-$ | 2-cyanophenyl | (oil) |
| Me | $-(CH_2)_3NHCH_2C(CH_3)_2-$ | phenyl | (oil) |
| Me | $-CH_2CH=CHCH_2-$ (trans) | phenyl | (oil) |
| Me | $-CH_2CH=CHCH_2-$ (trans) | 2-chlorophenyl | (oil) |
| Me | $-CH_2CH=CHCH_2-$ | 2-methoxyphenyl | (oil) |

TABLE I-continued

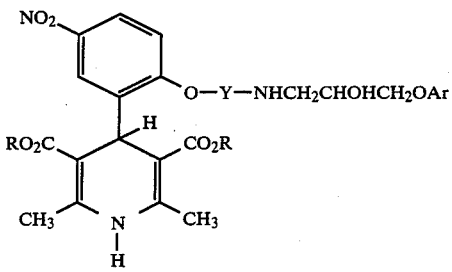

| R | Y | Ar | m.p. (°C.) |
|---|---|----|------------|
|   |   |    | (trans)    |

TABLE 2

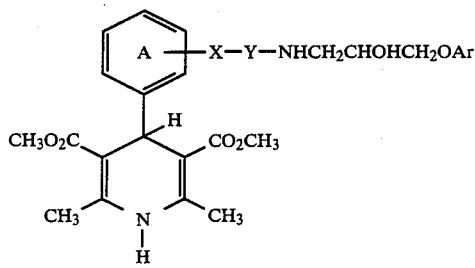

| Ring A and positions of chain | X | Y | Ar | m.p. (°C.) |
|---|---|---|---|---|
| 3-nitro-4- | O | (CH$_2$)$_3$ | 2-methoxyphenyl | (oil) |
| 3-nitro-4- | O | (CH$_2$)$_4$ | 2-methoxyphenyl | 77–82 |
| 2- | O | (CH$_2$)$_4$ | phenyl | (oil) |
| 5-nitro-2- | S | (CH$_2$)$_3$ | 2-chlorophenyl | 149–152 |
| 5-nitro-2- | S | (CH$_2$)$_3$ | 2-methoxyphenyl | 126–130 |

The pyridinedicarboxylate starting materials were prepared by a similar process to that described in the second part of Example 3. Those intermediates and starting materials which were characterised by melting point are shown in the following tables:

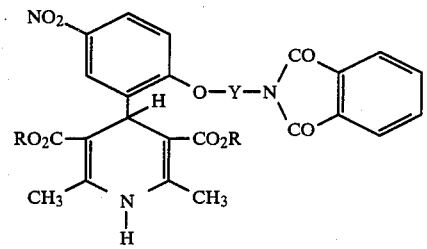

| Y | m.p. (°C.) |
|---|---|
| (CH$_2$)$_3$ | 193–196 |
| (CH$_2$)$_5$ | 132–134 |
| (CH$_2$)$_6$ | 99–102 |
| (CH$_2$)$_7$ | 88–90 |
| CH$_2$(1,4-phenylene)CH$_2$CH$_2$ | 190–193 |
| CH$_2$(1,2-phenylene)CH$_2$CH$_2$ | 155–158 |
| CH$_2$CH=CHCH$_2$(trans) | 129–132 |

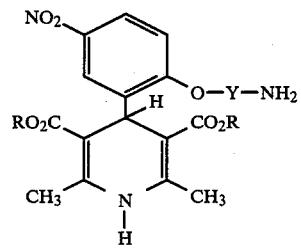

| Y | m.p. (°C.) |
|---|---|
| (CH$_2$)$_4$ | 84–86 |

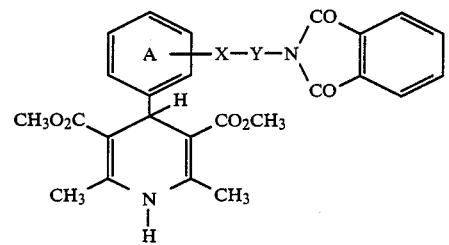

| R | Y | m.p. (°C.) | Note |
|---|---|---|---|
| Et | (CH$_2$)$_3$ | 235–238 |  |
| Et | (CH$_2$)$_4$ | 169–173 |  |
| Et | (CH$_2$)$_5$ | 188–192 |  |
| Et | (CH$_2$)$_6$ | 188–191 |  |
| Et | (CH$_2$)$_7$ | 158–161 |  |
| Me | CH$_2$(1,4-phenylene)CH$_2$CH$_2$ | 224–228 | 1 |
| Me | CH$_2$(1,3-phenylene)CH$_2$CH$_2$ | 244–248 | 1 |
| Me | CH$_2$(1,2-phenylene)CH$_2$CH$_2$ | 145–148 | 1 |
| Me | CH$_2$(1,4-phenylene)OCH$_2$CH$_2$ | 232–234 | 1 |
| Me | CH$_2$(1,3-phenylene)O(CH$_2$)$_3$ | 175–180 |  |
| Me | CH$_2$CH=CHCH$_2$(trans) | 203–205 |  |

| Ring A and position of side chain | X | Y | m.p. (°C.) | Note |
|---|---|---|---|---|
| 3-nitro-4- | O | (CH$_2$)$_3$ | 195–198 | 1,2 |
| 3-nitro-4- | O | (CH$_2$)$_4$ | 178–181 | 1,2 |
| 2- | O | (CH$_2$)$_4$ | 191–193 |  |
| 5-nitro-2- | S | (CH$_2$)$_3$ | 213–216 | 1 |

| R | Y | m.p. (°C.) | Note |
|---|---|---|---|
| Et | (CH$_2$)$_4$ | 180–184 |  |

| | | -continued | |
|---|---|---|---|
| Et | (CH$_2$)$_5$ | 138–140 | |
| Et | (CH$_2$)$_6$ | 175–177 | |
| Me | (CH$_2$)$_7$ | 174–176 | |
| Me | CH$_2$(1,4-phenylene)-CH$_2$CH$_2$ | 188–190 | |
| Me | CH$_2$(1,2-phenylene)-CH$_2$CH$_2$ | 236–239 | 3 |
| Me | CH$_2$CH=CHCH$_2$(trans) | 188–190 | |
| Me | (CH$_2$)$_4$ | 188–194 | 4 |
| Me | (CH$_2$)$_3$ | 194–197 | 3,5 |

Note 1
An extra molar proportion of methyl acetoacetate and a molar proportion of ammonium acetate were used in place of methyl 3-aminocrotonate in the synthesis of the dihydropyridine.

Note 2
The intermediate dimethyl 1,4-dihydro-4-(4-hydroxy-3-nitrophenyl)-2,6-dimethylpyridine-3,5-dicarboxylate had m.p. 200–201° C.

Note 3
The phthalimido group was removed by heating in ethanolamine solution at 100° C. for 1 hour.

Note 4
The 4-phenyl ring contains no NO$_2$ group.

Note 5
The 4-phenyl ring contains the group —S—Y—NH$_2$, not —O—Y—NH$_2$.

The aldehyde intermediate for the compound wherein —Y— is —CH$_2$CH$_2$C(CH$_3$)$_2$— was prepared by reacting 3-amino-3-methylbutan-1-ol with phthalic anhydride in refluxing dimethoxyethane, removal of water by heating in toluene in a Dean and Stark apparatus, and reacting the product obtained with 2-chloro-5-nitrobenzaldehyde in dimethylformamide in the presence of sodium hydride.

The intermediate for the compound wherein —Y— is —CH$_2$(1,3-phenylene)OCH$_2$CH$_2$CH$_2$— was prepared by reacting 5-nitrosalicylaldehyde with 3-acetoxybenzyl chloride, and then forming the dihydropyridine with methyl acetoacetate and ammonium acetate, the acetoxy group being hydrolysed during the reaction. Dimethyl 1,4-dihydro-4-[2-(m-hydroxybenzyloxy)-5-nitrophenyl]-2,6-dimethylpyridine-3,5-dicarboxylate has m.p. 261°–263° C.

The intermediates for reacting with 5-nitrosalicylaldehyde to prepare compounds wherein —Y— contains an ethylbenzyl or ethoxybenzyl group were prepared by the reduction of the appropriate methyl cyanomethylbenzoate or cyanomethoxybenzoate with diborane in tetrahydrofuran solution, followed by the reaction of the amino compound thus obtained with phthalic anhydride at 100° C. and then with phosphorus tribromide also at 100° C. The various intermediates which were characterised have melting points as follows: 4-(2-aminoethyl)benzyl alcohol hydrochloride m.p. 160°–162° C. 3-(2-aminoethyl)benzyl alcohol hydrochloride m.p. 115°–118° C. 2-(2-aminoethyl)benzyl alcohol hydrochloride m.p. 103°–104° C. 4-(2-aminoethoxy)benzyl alcohol m.p. 92°–94° C. 3-(2-aminoethoxy)benzyl alcohol hydrochloride m.p. 143°–145° C. 4-(2-phthalimidoethyl)benzyl bromide 158°–161° C. 3-(2-phthalimidoethyl)benzyl bromide 93°–94° C. 2-(2-phthalimidoethyl)benzyl bromide 140°–141° C. 3-(2-phthalimidoethoxy)benzyl bromide 116°–117° C. 4-(2-phthalimidoethoxy)benzyl chloride 109°–112° C. (prepared by reacting with mesyl chloride and triethylamine in place of phosphorus tribromide).

The aldehyde intermediate for the compound wherein —Y— is —(CH$_2$)$_3$NHCH$_2$C(CH$_3$)$_2$— was prepared by a similar process to that described in the second part of Example 6, initially from 5-nitrosalicylaldehyde and 1,3-dichloropropane, then reaction of the aldehyde obtained with methyl acetoacetate and ammonium acetate, and finally the reaction of the dimethyl 4-[2-(3-chloropropoxy)-5-nitrophenyl]-1,4-dihydro-2,6-dimethylpyridine-3,5-dicarboxylate thus obtained (m.p. 195°–197° C. after crystallisation from diethyl ether) with 2-amino-2-methylpropylamine.

The aldehyde intermediate for the compound wherein —X— is —S— was prepared from 2-chloro-5-nitrobenzaldehyde (0.93 g.), 3-phthalimidopropylthiol (1.105 g.) sodium hydride (0.24 g. of a 50% dispersion in oil) and dimethylformamide (25 ml.) at laboratory temperature. 5-Nitro-2-(3-phthalimidopropylthio)benzaldehyde has m.p. 166°–168° C. after crystallisation from ethyl acetate. The thiol itself (m.p. 47°–49° C.) was prepared from 3-bromopropylphthalimide and thiourea in refluxing ethanol, and hydrolysis of the 3-phthalimidopropylisothiouronium bromide (m.p. 228°–229° C.) thus obtained with refluxing aqueous 10% sodium carbonate solution.

EXAMPLE 5

The process described in Example 3 was repeated using either S-(+)- or R-(−)-1-phenyloxirane in place of phenylglycidyl ether. There were thus obtained as oils, the structures of which were confirmed by elemental analysis, mass spectroscopy and proton magnetic resonance spectroscopy respectively: (R)-(−)-dimethyl 1,4-dihydro-4-{2-[4-(2-hydroxy-2-phenylethylamino)butoxy]-5-nitrophenyl}-2,6-dimethylpyridine-3,5-dicarboxylate, [α]$_D^{25}$ = −9.9° (2% in methanol); and the corresponding (S)-(+)-isomer, [α]$_D^{25}$ = +10.35° (2% in methanol).

EXAMPLE 6

A molten mixture of 1-amino-3-phenoxypropan-2-ol (6.68 g.) and dimethyl 4-[2-(4-chlorobutoxy)-5-nitrophenyl]-1,4-dihydro-2,6-dimethylpyridine-3,5-dicarboxylate (9.05 g.) was stirred at 125°–135° C. for 30 minutes, cooled and dissolved in warm methylene chloride (100 ml.). The mixture was filtered and the filtrate was washed successively twice with aqueous 10% sodium bicarbonate solution and once with water (50 ml. each time), dried and evaporated to dryness. The residue was purified by flash chromatography on a silica gel (Merck 9385) column (800 g.) using a 90:10:3 v/v/v mixture of ethyl acetate, methanol and aqueous ammonia solution (specific gravity 0.88) as eluent. The product was crystallised from a mixture of ethyl acetate and petroleum ether (b.p. 60°–80° C.) and there was thus obtained dimethyl 1,4-dihydro-4-{2-[4-(2-hydroxy-3-phenoxypropylamino)butoxy]-5-nitrophenyl}-2,6-dimethylpyridine-3,5-dicarboxylate, m.p. 122°–124° C.

The dimethyl pyridine-3,5-dicarboxylate (m.p. 204°–206° C.) used as starting material was obtained by a similar process to that described in the second part of Example 3, using 5-nitrosalicylaldehyde (16.7 g.), potassium carbonate (13.8 g.), 1,4-dichlorobutane (25.4 g.) and diemthylformamide (300 ml.) as initial starting materials, and the 2-(4-chlorobutoxy)-5-nitrobenzaldehyde thus obtained (3.0 g., m.p. 51°–52° C.), methyl acetoacetate (2.7 g.), ammonium acetate (1.0 g.) and ethanol (30 ml.) as reactants in the subsequent reaction (the ammonium acetate and part of the methyl acetoacetate being equivalent to methyl 3-aminocrotonate).

The process described above was repeated using the appropriate pyridine-3,5-dicarboxylate ester and the appropriate 1-amino-3-aryloxypropan-2-ol as starting materials and there were thus obtained the compounds described in the following table:

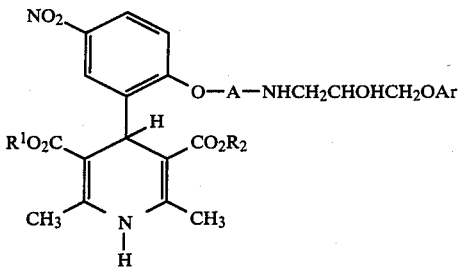

| $R^1$ | $R^2$ | A | Ar | m.p.(°C.) | Note |
|---|---|---|---|---|---|
| methyl | methyl | $(CH_2)_4$ | phenyl | 158–163 | 1 |
| methyl | methyl | $(CH_2)_4$ | phenyl | 162–165 | 2 |
| methyl | methyl | $(CH_2)_4$ | 2-methoxy-phenyl | 130–132.5 | |
| methyl | ethyl | $(CH_2)_4$ | phenyl | (oil) | 3 |
| methyl | ethyl | $(CH_2)_4$ | 2-chlorophenyl | 111–112 | 3 |
| methyl | ethyl | $(CH_2)_4$ | 2-cyanophenyl | 160–163 | 3 |
| methyl | ethyl | $(CH_2)_4$ | 2-methoxyphenyl | (oil) | 3 |
| isobutyl | isobutyl | $(CH_2)_4$ | phenyl | 122–125 | |
| allyl | allyl | $(CH_2)_4$ | phenyl | 142–143 | |
| allyl | allyl | $(CH_2)_4$ | 2-cyanophenyl | 141–145 | |
| allyl | allyl | $(CH_2)_4$ | 2-methoxyphenyl | 116–118 | |
| methyl | methyl | $(CH_2)_2O(CH_2)_2$ | phenyl | (oil) | 4 |
| methyl | methyl | $(CH_2)_4O(CH_2)_4$ | phenyl | (oil) | 5 |
| methyl | methyl | $(CH_2)_4O(CH_2)_4$ | 2-methoxyphenyl | (oil) | 5 |
| methyl | methyl | $(CH_2)_4NH(CH_2)_2$ | phenyl | (oil) | 6 |
| methyl | methyl | $CH_2CH=CHCH_2$(cis) | phenyl | 106–110 | 7 |
| methyl | methyl | $CH_2CH=CHCH_2$(cis) | 2-methoxyphenyl | (oil) | 7 |

Note 1 (−)-isomer, $[\alpha]_D^{25} = -8.3°$ (2% of hydrochloride in methanol).

Note 2 (+)-isomer, $[\alpha]_D^{25} = +9.6°$ (2% of hydrochloride in methanol).

The (−)-isomer was obtained by using (+)-1-amino-3-phenoxypropan-2-ol as starting material, and the (+) isomer was obtained by using (−)-1-amino-3-phenoxypropan-2-ol as starting material.

Note 3 The ethyl 4-[2-(4-chlorobutoxy)-5-nitrophenyl]-1,4-dihydro-5-methoxycarbonyl-2,6-dimethylpyridine-3-carboxylate (m.p. 157–158° C.) used as starting material was prepared from 2-(4-chlorobutoxy)-5-nitrobenzaldehyde (0.6 g.), ethyl acetoacetate (0.3 g.), methyl-3-aminocrotonate (0.27 g.) and ethanol (40 ml.) by a similar process to that described in the third paragraph of Example 3.

Note 4
The reaction was carried out in dimethylformamide solution at 100° C. for 3 hours, and the pyridine starting material was dimethyl 1,4-dihydro-2,6-dimethyl-4-{5-nitro-2-[(2-tosyloxyethoxy)ethoxy)]phenyl}pyridine-3,5-dicarboxylate, which was prepared from 5-nitrosalicylaldehyde (0.83 g.), potassium carbonate (1.1 g.) bis-2-tosyloxyethyl ether (2.28 g.) and dimethylformamide (20 ml.), and then the aldehyde thus obtained (0.56 g.), methyl acetoacetate (3.5 g.), ammonium acetate (0.12 g.) and isopropanol (10 ml.).

Note 5
The starting material dimethyl 4-{2-[4-(4-chlorobutoxy]-5-nitrophenyl}-1,4-dihydro-2,6-dimethylpyridine-3,5-dicarboxylate (m.p. 143–144° C. after crystallisation from ethanol) was prepared as described in the second paragraph above, using bis-4-chlorobutyl ether in place of 1,4-dichlorobutane.

Note 6
The propanol starting material was 1-(2-aminoethylamino)-3-phenoxypropan-2-ol.

Note 7
The starting material dimethyl 4-[2-(4-chlorobut-cis-2-enyloxy)-5-nitrophenyl]-1,4-dihydro-2,6-dimethylpyridine-3,5-dicarboxylate (m.p. 181–183° C. after crystallisation from ethanol) was prepared as described in the second paragraph above, using 1,4-dichloro-cis-but-2-ene in place of 1,4-dichlorobutane.
The intermediate 2-(4-chlorobut-cis-2-enyloxy)-5-nitrobenzaldehyde has m.p. 56–57° C.

The other pyridine starting materials were prepared as described in the second paragraph above using the appropriate acetoacetate ester in place of methyl acetoacetate. Diallyl 4-[2-(4-chlorobutoxy)-5-nitrophenyl]-1,4-dihydro-2,6-dimethylpyridine-3,5-dicarboxylate has m.p. 144°–146° C. and the corresponding diisobutyl compound has m.p. 141°–151° C.

EXAMPLE 7

A solution of (±)-dimethyl 1,4-dihydro-4-{2-[4-(2-hydroxy-3-phenoxypropylamino)butoxy]-5-nitrophenyl}-2,6-dimethylpyridine-3,5-dicarboxylate (Example 3; 0.01 g.) in methanol (1 ml.) was injected onto a high performance liquid chromatograph column (25 cm.×2.12 cm.) containing silica ('Zorbax' quality) which had previously been equilibrated with a 58:42 v/v mixture of isopropanol and hexane in which were dissolved (+)-tartaric acid (0.01 molar) and pyridine (0.05% by volume). The column was eluted with the equilibrating solvent mixture, the product being detected by ultraviolet absorption at 300 nm. The two separated products from two such elutions were individually combined and partitioned between ethyl acetate (15 ml.) and saturated aqueous sodium bicarbonate solution (20 ml.). The organic layer was separated, washed twice with saturated aqueous sodium chloride solution, dried and evaporated to dryness. There were thus obtained as oils:

(a) as less polar isomer, eluted first, (−)-dimethyl 1,4-dihydro-4-{2-[4-(2-hydroxy-3-phenoxypropylamino)butoxy]-5-nitrophenyl}-2,6-dimethylpyridine-3,5-dicarboxylate, $[\alpha]_D^{20} = -11.1°$ (c, 0.87% in an 0.26N-solution of hydrochloric acid in methanol); and (b) as more polar isomer, eluted second, the corresponding (+)-isomer. $[\alpha]_D^{20} = +11.6°$ (C, 0.47% in an 0.26N solution of hydrochloric acid in methanol).

The process described above was repeated to separate the isomers of (±)-dimethyl 1,4-dihydro-4-{2-[4-(2-hydroxy-3-o-methoxyphenoxypropylamino)butoxy]-5-nitrophenyl}-2,6-dimethylpyridine-3,5-dicarboxylate, the (−)-isomer having $[\alpha]_D^{20} = -7.2°$ (C, 0.6% in an 0.26N solution of hydrochloric acid in methanol) and the (+)-isomer having $[\alpha]_D^{20} = +6.1°$ (C=0.35% in the same solution).

What we claim is:

1. A dihydropyridine of the formula:

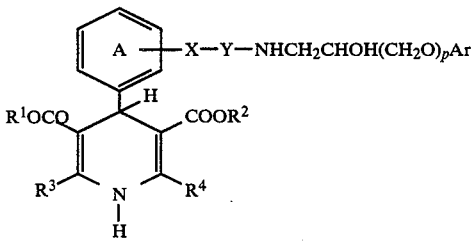

wherein $R^1$ and $R^2$, which may be the same or different, each is alkyl or alkoxyalkyl each of up to 6 carbon atoms; wherein $R^3$ and $R^4$, which may be the same or different, each is alkyl of up to 6 carbon atoms;

wherein benzene ring A bears one or more additional substituents selected from halogeno, cyano, nitro, trifluoromethyl and alkyl of up to 6 carbon atoms, wherein Ar is phenyl, naphthyl, tetrahydronaphthyl, indanyl or indenyl which is unsubstituted or which bears one or more substituents selected from halogeno, trifluoromethyl, hydroxy, amino, nitro, carbamoyl and cyano, and alkyl, alkenyl, alkoxy, alkenyloxy, alkoxyalkoxy, alkylthio, alkanoyl, carbamoylalkyl and alkanoylamino each of up to 6 carbon atoms;

wherein p is 0 or 1;

wherein X is —O— or —S—; and wherein Y is a group of the formula —$(CH_2)_mC(CH_3)_2$— wherein m is 2, 3, 4 or 5, or an acid-addition salt thereof.

2. A dihydropyridine as claimed in claim 1 wherein $R^1$ and $R^2$, which may be the same or different, each is alkyl of up to 4 carbon atoms, wherein $R^3$ and $R^4$ are both methyl, wherein the benzene ring A bears a nitro substituent, wherein Ar is phenyl which is unsubstituted or which bears one or two substituents selected from fluoro, chloro, bromo, hydroxy, nitro, cyano, alkyl, alkenyl, alkoxy, alkenyloxy and alkanoyl each of up to 4 carbon atoms, wherein p is 0 or 1, wherein X is —O— or —S— and wherein Y is as stated in claim 1, or an acid-addition salt thereof.

3. A dihydropyridine as claimed in claim 2 wherein $R^1$ and $R^2$, which may be the same or different, each is methyl or ethyl, wherein $R^3$ and $R^4$ are both methyl, wherein the benzene ring A bears a nitro substituent in the 5-position and the side-chain in the benzene ring A is in the 2-position, wherein Ar is phenyl which is unsubstituted or which bears a single fluoro, chloro, bromo, nitro, cyano, allyl, methoxy, ethoxy, propoxy, isopropoxy, allyloxy or acetyl substituent in the 2-position, wherein p is 1, wherein X is —O— and wherein Y is a group of the formula —$(CH_2)_mC(CH_3)_2$— wherein m is 2, 3, 4 or 5, or an acid-addition salt thereof.

4. A dihydropyridine as claimed in claim 3 wherein $R^1$, $R^2$, $R^3$ and $R^4$ are all methyl, wherein the benzene ring A bears a nitro substituent in the 5-position and the side-chain in the benzene ring A is in the 2-position, wherein Ar is 2-cyanophenyl, wherein p is 1, wherein X is —O— and wherein Y is —$(CH_2)_3C(CH_3)_2$—, or an acid-addition salt thereof.

5. The compound dimethyl 1,4-dihydro-4-{2-[3-(2-hydroxy-3-phenoxypropylamino)-3-methylbutoxy]-5-nitrophenyl}-2,6-dimethylpyridine-3,5-dicarboxylate having the formula:

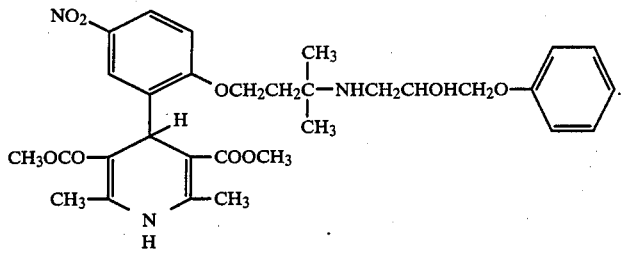

6. An (S)-enantiomer of the compound claimed in claim 5, in respect of the asymmetrical carbon atom at the 2-position of the (2-hydroxy-3-(optionally-substituted)phenoxypropylamino)-group.

7. The compound diethyl 4-[2-(N-{N-[2-(3-0-cyanophenoxy-2-hydroxypropylamino)ethyl]carbamoylmethyl}carbamoylmethoxy-5-nitrophenyl]-1,4-dihydro-2,6-dimethylpyridine-3,5-dicarboxylate having the formula:

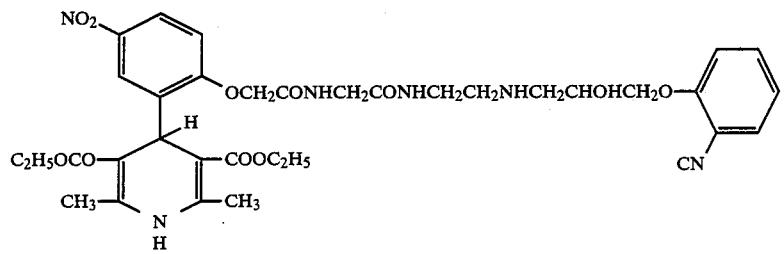

8. The compound dimethyl 1,4-dihydro-4-(2-3-[2-(2-hydroxy-3-o-methoxyphenoxypropylamino)ethoxy]-benzyloxy-5-nitrophenyl)-2,6-dimethylpyridine-3,5-dicarboxylate having the formula:

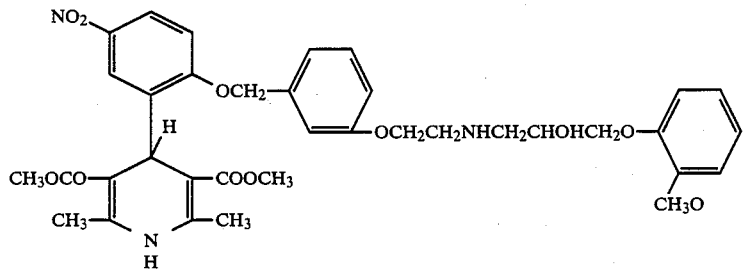

9. An (S)-enantiomer of a compound claimed in claim 7 or 8, in respect of the asymmetrical carbon atom at the 2-position of the (2-hydroxy-3-(optionally-substituted)-phenoxypropylamino)-group.

10. A pharmaceutical composition comprising as active ingredient at least one dihydropyridine, claimed in claim 1, or an acid-addition salt thereof in an amount sufficient to elicit an antihypertensive effect, in association with a pharmaceutically-acceptable diluent or carrier therefor.

11. A pharmaceutical composition comprising as active ingredient at least one dihydropyridine, claimed in claim 7 or claim 8 or an acid-addition salt thereof, in an amount sufficient to elicit an antihypertensive effect, in association with a pharmaceutically-acceptable diluent or carrier therefor.

12. A method for the treatment of angina pectoris, cardiac arrhythmias or hypertension in a warm-blooded animal which comprises administering to said animal an effective amount of the compound claimed in claim 1.

13. A method for the treatment of heart disease or hypertension in a warm-blooded animal which comprises administering to said animal an effective amount of a compound claimed in claim 7 or claim 8.

* * * * *